United States Patent
Fujii et al.

(10) Patent No.: US 7,817,256 B2
(45) Date of Patent: Oct. 19, 2010

(54) PERSONAL AUTHENTICATION METHOD AND PERSONAL AUTHENTICATION DEVICE UTILIZING FINGER-TIP BLOOD FLOW MEASUREMENT BY LASER LIGHT

(75) Inventors: Hitoshi Fujii, Munakata (JP); Naoki Konishi, Kaho-gun (JP)

(73) Assignee: Kyushu Institute of Technology, Fukuoka (JP)

( * ) Notice: Subject to any disclaimer, the term of this patent is extended or adjusted under 35 U.S.C. 154(b) by 235 days.

(21) Appl. No.: 12/280,035

(22) PCT Filed: Jan. 9, 2007

(86) PCT No.: PCT/JP2007/050060

§ 371 (c)(1),
(2), (4) Date: Aug. 20, 2008

(87) PCT Pub. No.: WO2007/097129

PCT Pub. Date: Aug. 30, 2007

(65) Prior Publication Data

US 2010/0168585 A1 Jul. 1, 2010

(30) Foreign Application Priority Data

Feb. 22, 2006 (JP) .............................. 2006-044989

(51) Int. Cl.
*G06K 9/74* (2006.01)
(52) U.S. Cl. .......................................... 356/71; 356/39
(58) Field of Classification Search .................. 356/39, 356/71
See application file for complete search history.

(56) References Cited

U.S. PATENT DOCUMENTS 5,339,817 A * 8/1994 Nilsson ...................... 600/473
7,447,408 B2 * 11/2008 Bouma et al. ............... 385/123

FOREIGN PATENT DOCUMENTS

| JP | 2-5190 A | 1/1990 |
|---|---|---|
| JP | 4-242628 A | 8/1992 |
| JP | 5-28133 B2 | 4/1993 |
| JP | 5-28134 82 | 4/1993 |
| JP | 5-73666 B2 | 10/1993 |
| JP | 8-16752 A | 1/1996 |
| JP | 8-112262 A | 5/1996 |

(Continued)

*Primary Examiner*—Roy Punnoose
(74) *Attorney, Agent, or Firm*—Sughrue Mion, PLLC

(57) ABSTRACT

A personal authentication method is provided that includes imaging, on an image sensor as a laser speckle using an optical system, light reflected from a blood vessel layer in subcutaneous and internal tissues when a laser beam is expanded and made to irradiate a finger pad, calculating a quantity that represents the rate of change with respect to time of the amount of light received for each pixel of the laser speckle, obtaining a finger pad blood flow map as a two-dimensional map of the numerical values, and comparison-checking the blood flow map against pre-registered data of individuals, wherein using a near-infrared laser beam or using this in combination with a visible laser beam, comparison-checking against pre-registered data of individuals is carried out using a pattern reflecting a fingerprint occurring within the finger pad blood flow map obtained from reflected light and, observed superimposed thereon, an internal tissue blood flow distribution pattern, and there is also provided a device used for the method.

4 Claims, 3 Drawing Sheets

FOREIGN PATENT DOCUMENTS

Figure 1:
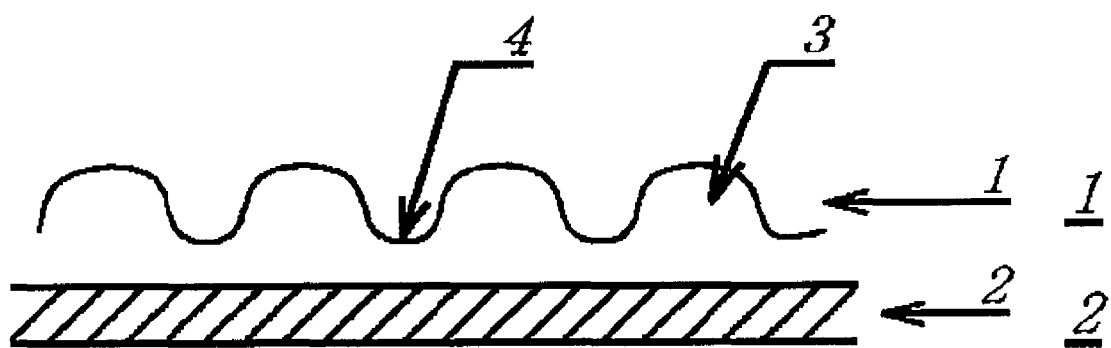

| | | |
|---|---|---|
| JP | 2003-85538 A | 3/2003 |
| JP | 2003-164431 A | 6/2003 |
| JP | 2003-180641 A | 7/2003 |
| JP | 2003-527906 A | 9/2003 |
| JP | 2003-331268 A | 11/2003 |
| JP | 2004-290664 A | 10/2004 |
| JP | 2004-326820 A | 11/2004 |
| JP | 2005-527874 A | 9/2005 |
| WO | 03/025836 A1 | 3/2003 |
| WO | 2005/122896 A1 | 12/2005 |

* cited by examiner

PERSONAL AUTHENTICATION METHOD AND PERSONAL AUTHENTICATION DEVICE UTILIZING FINGER-TIP BLOOD FLOW MEASUREMENT BY LASER LIGHT

TECHNICAL FIELD

The present invention relates to a personal authentication method and a personal authentication device utilizing finger-tip blood flow measurement and, more particularly, to a personal authentication method and device in which blood flow in subcutaneous and internal tissues of a finger-tip is measured using a laser beam with a specific wavelength.

BACKGROUND ART

With regard to personal authentication using a fingerprint, various systems have so far been developed which, instead of the old-established method involving visual inspection, a laser, etc. is used and a pattern is inputted into a computer as an image and analyzed. A large number of techniques for a sensor section for detecting a fingerprint have been proposed; for example, an optical method in which a fingerprint pattern is directly captured into an image sensor by combining differences in scattering angle between peak and valley with total reflection conditions, and a method in which a pattern is extracted by utilizing a semiconductor sensor that detects differences in charge distribution on a contact face have been put into practice. Furthermore, a method in which personal authentication is carried out by extracting a vein pattern of a finger-tip or a palm of a hand by means of near-infrared light has been proposed, and commercialization thereof is underway. However, none of these methods is yet perfect, and the fight against forgery is continuing.

(Patent Publication 1) JP-A-5-73666 (JP-A denotes a Japanese unexamined patent application publication)
(Patent Publication 2) JP-A-8-16752
(Patent Publication 3) JP-A-2003-331268

On the other hand, it is known that, when a laser is shone on a living body, the intensity distribution of reflected scattered light forms a dynamic laser speckle (random spot pattern) due to moving scattering particles such as blood cells; this pattern is detected on an imaging plane by an image sensor, and by quantifying changes over time of the pattern in each pixel and displaying them as a map, it is possible to image the blood flow distribution of capillary vessels in the vicinity of the surface of the living body. Using such a phenomenon, techniques and devices for measuring a blood flow map of the area underneath the skin or of the ocular fundus have been proposed by the present inventors.

(Patent Publication 4) JP-B-5-28133 (JP-B denotes a Japanese examined patent application publication)
(Patent Publication 5) JP-B-5-28134
(Patent Publication 6) JP-A-4-242628
(Patent Publication 7) JP-A-8-112262
(Patent Publication 8) JP-A-2003-164431
(Patent Publication 9) JP-A-2003-180641

The present inventors have carried out an intensive investigation into the concept of combining a blood flow map and a fingerprint pattern and its use for personal authentication, and have already proposed a personal authentication method involving measuring subcutaneous blood flow and means therefor. That is, there have been proposed a personal authentication method comprising (1) a step of imaging, on an image sensor as a laser speckle using an optical system, light reflected from a subcutaneous blood vessel layer when a laser beam is expanded and made to irradiate a finger pad, (2) a step of determining a quantity that represents the rate of a change with respect to time of the amount of light received for each pixel of the laser speckle, for example, the average rate of change with respect to time, or the reciprocal of the magnitude of the variation in the amount of light received integrated over the exposure time of the image sensor, and obtaining a finger pad blood flow map as a two-dimensional map of numerical values thereof, and (3) a step of comparing and evaluating a fingerprint pattern represented as a blood flow map against pre-registered data of individuals, and devices for carrying out each step (Patent Publication 10).

(Patent Publication 10) International Patent Application WO2005/122896

It has been found that, since fingerprint patterns have complicated shapes compared with vein patterns, the methods and devices for personal authentication in the above-mentioned proposals can achieve authentication with considerable accuracy. However, there is a possibility that more sophisticated crimes such as, for example, smoothing a fingerprint using a chemical, etc., and affixing thereto a thin sheet having projections and recesses imitating a fingerprint of another person, cannot be prevented sufficiently. It is thus necessary to develop a more stringent personal authentication method and device for applications where more powerful prevention of crime is necessary.

DISCLOSURE OF INVENTION

Problems to be Solved by the Invention

The present inventors have continued research in order to solve the above-mentioned problems and develop a personal authentication method and a device having higher accuracy, and have found a method and means in which a finger-tip is irradiated with one laser beam at a specific wavelength or with a plurality of different laser beams at specific wavelengths at the same time or in sequence, and superimposed blood flow rate maps or a plurality of blood flow rate maps with respect to reflected light are obtained. The depth of penetration of a laser into tissue depends on the wavelength of the laser; with light having a short wavelength such as visible light, only a blood flow distribution close to the surface, that is, a fingerprint pattern, is obtained, but since light having a long wavelength such as near-infrared light enters deep into the tissue, a blood flow map reflecting a blood flow distribution in the interior can be obtained. There is a difference in blood flow distribution in the interior between individuals, and since it is difficult to forge, if this is added to authentication data the accuracy of personal verification is improved due to a synergistic effect.

Means for Solving the Problems

Among the present inventions, the invention described in the original claim 1 (hereinafter, the same applies to claims 2 to 6) is a personal authentication method comprising imaging, on an image sensor as a laser speckle using an optical system, light reflected from a blood vessel layer in subcutaneous and internal tissues when a laser beam is expanded and made to irradiate a finger pad, calculating a quantity that represents the rate of change with respect to time of the amount of light received for each pixel of the laser speckle, obtaining a finger pad blood flow map as a two-dimensional map of the numerical values, and comparison-checking the blood flow map against pre-registered data of individuals, wherein using a near-infrared laser beam, which can reach the internal tissue of the finger pad, a finger pad blood flow map obtained from reflected light is measured, and comparison-checking against pre-registered data of individuals is carried out using in combination a pattern reflecting a fingerprint occurring within the blood flow map and, observed superimposed thereon, an internal tissue blood flow distribution pattern.

In the invention described in claim 1, the near-infrared laser light preferably has a wavelength in the range of about 770 to 1200 nm (claim 2).

Among the present inventions, the invention described in claim 3 is a personal authentication method comprising imaging, on an image sensor as a laser speckle using an optical system, light reflected from a blood vessel layer in subcutaneous and internal tissues when a laser beam is expanded and made to irradiate a finger pad, calculating a quantity that represents the rate of change with respect to time of the amount of light received for each pixel of the laser speckle, obtaining a finger pad blood flow map as a two-dimensional map of the numerical values, and comparison-checking the blood flow map against pre-registered data of individuals, wherein using a near-infrared laser beam, which can reach the internal tissue of the finger pad, and a visible laser beam, which is easily absorbed by the subcutaneous stratum corneum, finger pad blood flow maps obtained from the respective reflected lights are measured at the same time or in sequence, and the two types of blood flow maps thus obtained are comparison-checked against pre-registered data of individuals.

In the invention described in claim 3, the near-infrared laser light preferably has a wavelength in the range of about 770 to 1200 nm (claim 4). Furthermore, the visible laser light preferably has a wavelength in the range of about 380 to 770 nm (claim 5).

Among the present inventions, the invention described in claim 6 is a personal authentication device comprising one or two irradiating means that expand a laser beam and irradiate a finger pad, light-receiving means that has a large number of pixels and receives light reflected from a blood vessel layer beneath the finger pad, storage means that stores the output of each of the pixels obtained by the light-receiving means, calculating means that calculates a quantity representing the rate of change with respect to time of the amount of light received for each pixel using stored contents of the storage means, second storage means that stores a two-dimensional distribution of the calculation results obtained for each of the pixels as a blood flow map, and means for comparing and evaluating the blood flow map stored by the second storage means against pre-registered data of individuals.

EFFECTS OF THE INVENTION

The method already proposed by the present inventors (see Patent Publication 10), that is, a personal authentication method in which a fingerprint pattern is drawn using blood flow information characteristic of a living body, and the two-dimensional pattern thus obtained is comparison-checked against pre-registered data of individuals, is an excellent authentication method for which imitation or forgery is difficult, but the present invention provides an authentication system that is stronger than such a method. That is, in accordance with the invention of claim 1, since by using a near-infrared laser beam, which reaches internal tissue of a finger pad, a blood flow distribution pattern of the internal tissue is obtained in addition to a fingerprint pattern and superimposed thereon, by comparison-checking the two patterns against pre-registered data of individuals, a powerful personal authentication method is provided. Furthermore, in accordance with the invention of claim 3, there is provided a powerful personal authentication method in which by using a near-infrared laser beam, which can reach internal tissue of a finger pad, and a visible laser beam, which is easily absorbed by the subcutaneous stratum corneum, and measuring finger pad blood flow maps obtained from the respective reflected lights at the same time or in sequence, two types of blood flow maps are obtained, and they are comparison-checked against pre-registered data of individuals. Moreover, in accordance with the invention of claim 6, a personal authentication device for carrying out the above method is provided.

BRIEF DESCRIPTION OF DRAWINGS (FIG. 1) An explanatory diagram showing a cross section of skin of a finger pad.

(FIG. 2) A diagram of a blood flow map showing a fingerprint pattern in the present invention.

(FIG. 3) A diagram showing a blood flow map of a fingerprint and, superimposed thereon, a blood flow map unevenness state in the present invention.

Figure 3:
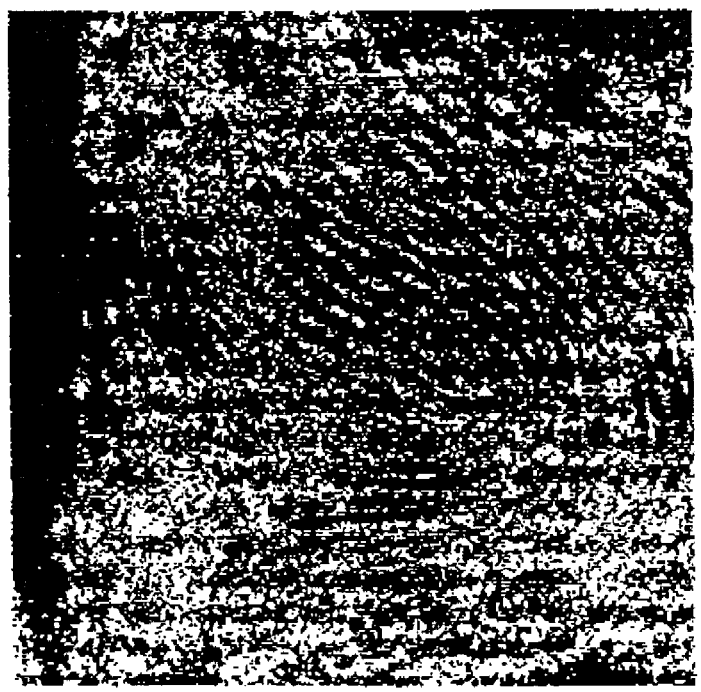

(FIG. 4) A diagram for explaining one example of a method for analyzing data obtained in FIG. 3.

(FIG. 5) A diagram showing one example of the device of the present invention.

EXPLANATION OF REFERENCE NUMERALS AND SYMBOLS

1 Stratum corneum
2 Subcutaneous blood vessel layer
3 Stratum corneum peak portion
4 Stratum corneum valley portion
5 Near-infrared semiconductor laser
6 Irradiation optical system
7 Finger pad
8 Laser spot
9 Imaging lens
10 Image sensor
11 Analytical personal computer
12 Display
13 Finger pad blood flow map
14 Visible light semiconductor laser

BEST MODE FOR CARRYING OUT THE INVENTION

Among biometric information, information obtained from blood flow has the characteristic that authentication cannot be carried out unless a sensor is operated by a living person. The present invention measures the blood flow of subcutaneous and internal tissues, which is spatially modulated due to projections and recesses of a fingerprint, by a blood flow measurement technique employing laser scattering, and in order to measure the blood flow of subcutaneous and internal tissues, firstly, a laser beam is expanded and made to irradiate a finger pad, and light reflected from a blood vessel layer present in the subcutaneous and internal tissues is imaged as a laser speckle on an image sensor using an optical system. The laser speckle is scanned continuously using an image sensor, a quantity representing the rate of change with respect to time of the amount of light received for each pixel, for example, the average change over time, or the reciprocal of the magnitude of the variation in the amount of light received integrated over the exposure time of the image sensor is calculated, and the numerical values thus obtained are converted into a two-dimensional map, thus giving a blood flow map of the finger pad. By comparison-checking this blood flow map against pre-registered data of individuals, authentication of an individual becomes possible.

One of the methods of the present invention is the personal authentication method wherein a laser beam having a long wavelength, which can reach the internal tissue of the finger pad, specifically a near-infrared laser beam, is used to measure a finger pad blood flow map obtained from light reflected thereon, and comparison-checking against pre-registered data of individuals is carried out. Another method is a method wherein a near-infrared laser beam and a laser beam having a shorter wavelength than this, specifically a visible laser beam, are used in combination, finger pad blood flow maps obtained from the respective reflected lights are measured at the same time or in sequence, and the two types of blood flow maps thus superimposingly obtained are comparison-checked against pre-registered data of individuals.

When a laser beam having a relatively short wavelength such as visible light is expanded and made to irradiate a finger pad, an irradiated spot is imaged on an image sensor using an optical system, and a blood flow rate map is obtained by measuring the change over time of an interference pattern formed on an image face for each pixel, due to the phenomenon of the blood flow rate being high for a section of a finger where the stratum corneum is thin, a fingerprint pattern can be extracted. On the other hand, since laser light having a relatively long wavelength such as near-infrared light can detect variation in the blood flow value of subcutaneous internal tissue of a finger-tip, by utilizing the positional relationship of portions where the blood flow value is high, or the positional relationship of portions where the change over time in blood flow value is large, personal authentication can be carried out. One of the present inventions constructs a personal authentication method having higher accuracy by combining the above-mentioned two phenomena.

A blood flow map of a finger pad obtained from reflected light of a visible laser beam mainly comprises a fingerprint pattern by light reflected from a subcutaneous capillary blood vessel layer. As a visible laser beam, one of about 380 to 770 nm can be used, but one of about 600 to 700 nm is preferable, and one of about 630 to 650 nm is particularly preferable since it is absorbed well by the stratum corneum.

A blood flow map of a finger pad obtained by reflected light of a near-infrared laser beam is mainly a sea-island like pattern characteristic of an individual, given by light reflected from blood vessels present in subcutaneous internal tissue. As a near-infrared laser beam that can reach internal tissue of a finger pad, one having about 770 to 1200 nm is normally used, one of about 800 to 900 nm is preferable, and one having a wavelength of about 830 to 850 nm is particularly preferable when the sensitivity of the image sensor is taken into consideration.

Figure 2:

The principle of the present invention is explained in detail below by reference to drawings. FIG. 1 is a cross-sectional diagram of skin of finger pad, 1 denotes the stratum corneum, 2 denotes a subcutaneous blood vessel layer, 3 denotes a peak portion of the stratum corneum, and 4 denotes a valley portion of the stratum corneum. In the present invention, for example, when a finger pad is irradiated with a laser having a wavelength of 650 nm, at this wavelength the laser light is easily absorbed by the peak portion 3 of the stratum corneum 1 of the finger in FIG. 1, and since subcutaneous blood flow is observed through projections and recesses of the keratin forming the fingerprint, a high blood flow value is obtained as a streak along the valley 4. Since the blood vessel layer 2 immediately beneath the stratum corneum is a uniform layer of capillary blood vessels, a uniform fingerprint-shaped blood flow map is obtained. By subjecting this to binary processing, a fingerprint pattern as shown in FIG. 2 is obtained. A method using such a fingerprint pattern for personal authentication has already been proposed by the present inventors.

On the other hand, when a laser having a wavelength of 830 nm is used, it is not absorbed very much by the stratum corneum, the laser light reaches a subcutaneous deeper tissue layer, is then reflected, and returns to the surface. Since arteriole and venule blood vessels for supplying blood to the capillary blood vessel layer are present in various parts in the deep portion, when laser light hits there, a blood flow value higher than the surroundings is obtained. Because of this, the blood flow map thus obtained shows unevenness characteristic of an individual, and the unevenness is superimposed on the blood flow map of the fingerprint. The blood flow distribution of this internal tissue is not observed as lines as in blood vessels, but as shown in FIG. 3 it is observed as a sea-island like unevenness. Since FIG. 3 is a black and white drawing, it is represented only as a gray-scale, but in practice it may be displayed in colors according to the degree of unevenness. It is therefore possible to use a blood flow map from a fingerprint and, superimposed thereon, a blood flow map unevenness for personal authentication. This is the invention described in claim 1 among the present inventions.

Figure 4:
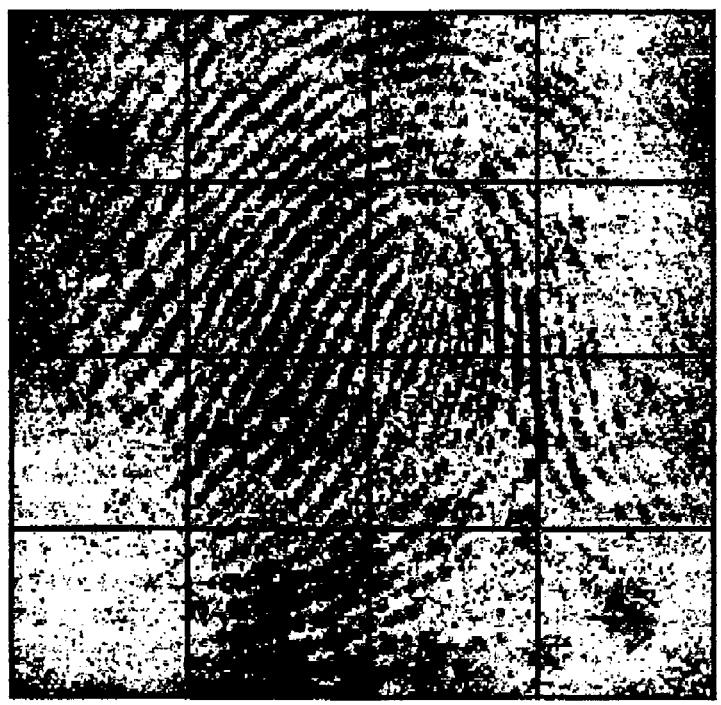

In the invention of claim 1, authentication may be carried out by, for example, dividing the blood flow map of FIG. 3 into 4×4=16 zones as shown in FIG. 4, reading in blood flow values of each region, and verifying them against a pre-registered distribution of values for each region of an individual.

Alternatively, authentication may be carried out by reading in blood flow values for each region of the 16 zones, determining the degree to which the value increases and decreases due to the pulse, and carrying out verification thereof against a pre-registered degree to which the value of an individual increases and decreases in each region.

On the other hand, the accuracy of authentication may be increased by combining the images of FIGS. 2 and 3, and this is the invention described in claim 3 of the present invention. For example, the map of FIG. 3 is divided into 4×4=16 zones as shown in FIG. 4, the average blood flow values of each zone are determined and arranged by putting them in order, such as (4,1), (4,4), etc., and this forms one type of authentication data. For each zone, for example, fingerprint data from the visible laser of FIG. 2 are analyzed with respect to the angle of orientation of a stripe pattern, the presence of branching points, etc. and if this is combined in an authentication operation, improved authentication accuracy can be exhibited due to a synergistic effect.

Alternatively, as in FIG. 4, authentication may be carried out by roughly dividing the finger blood flow map into, for example, 16 regions, reading in a blood flow value of each region, determining the degree to which the value increases and decreases due to the pulse, at the same time extracting characteristics of each region of the fingerprint pattern obtained using visible laser light, and verifying information of the two combined against pre-registered information for each region of an individual.

In the present invention, for example, light emitted from a small laser light source such as a semiconductor laser is expanded through an optical system, and made to irradiate a wide area of a finger pad. This irradiation spot is imaged on a light-receiving face of a CCD camera, etc. through a lens. Image signals obtained from the CCD camera are A/D converted and taken into a personal computer or a microcomputer, and a quantity representing the rate of change with respect to time of the amount of light received for each pixel, for example, the average rate of change with respect to time, or the reciprocal of the magnitude of the variation in the amount of light received integrated over the exposure time of the image sensor is calculated, and displayed as a map as necessary, thus giving blood flow map data. In the thus-obtained map of the blood flow of subcutaneous capillary blood vessels of the finger pad, a fingerprint pattern appears due to the above-mentioned action and principle. On the other hand, with regard to laser light that has reached a subcutaneous deep tissue layer, since arteriole and venule blood vessels for supplying blood to the capillary blood vessel layer are present in various parts in the deep portion, when laser light hits there, a blood flow value that is higher than that of the surroundings is obtained. Because of this, an unevenness characteristic of the individual is observed in the blood flow map so obtained, superimposed on the blood flow map from the fingerprint.

In accordance with the present invention, there is provided a device for carrying out a personal authentication method comprising the above-mentioned steps. The device of the present invention is a personal authorization device comprising one or two irradiating means that expand a laser beam and irradiate a finger pad, light-receiving means that has a large number of pixels and receives light reflected from the finger pad, storage means that stores the output of each pixel obtained by the light-receiving means, calculating means that calculates a quantity representing the rate of change with respect to time of the amount of light received for each pixel using the stored contents of the storage means, second storage means that stores a two-dimensional distribution of the calculation results obtained for each of the pixels as a blood flow map, and means for comparing and evaluating the blood flow map stored by the second storage means against pre-registered data of individuals. When a near-infrared laser beam and a visible laser beam irradiate at the same time, it is necessary to employ two irradiation means, but when they irradiate in sequence or when only a near-infrared laser beam irradiates, only one irradiation means is required.

As irradiation means, for example, light emitted from a semiconductor laser is expanded through a lens, and made to irradiate a wide region of a finger pad all at once. As light receiving means, an image sensor such as a line sensor or an area sensor is used. Electrical signals from the sensor are ND converted and then stored in a storage section of a microcomputer or a personal computer. Image signals are taken into the storage section continuously over a few seconds, the difference between two consecutive images is determined using a pre-set program in the microcomputer or the personal computer, and the rate of change with respect to time of the amount of light received is calculated. Alternatively, the rate of change with respect to time of the amount of light received is calculated by utilizing the blur rate of an image, that is, the property that, when the light intensity changes at high speed within the exposure time of an image sensor, signals are integrated, and instead the difference between the two images decreases. The calculation results may be displayed as a two-dimensional color map on a personal computer screen in accordance with the position of each pixel. Means for comparing and evaluating the values thus calculated or a blood flow map displayed on display means against a pre-registered blood flow map of an individual may employ various types of conventionally known means.

The method and the device of the present invention may additionally comprise a method/means for measuring a change in blood flow variation with respect to time, detecting the slope of the rise and the slope of the fall of a waveform, determining that the slope is steep on rising and gentle on falling, and detecting that it is a living finger. It is also possible to identify that is a living body by detecting the size of a region that changes over time accompanying the action of compressing and then releasing the base of the finger when carrying out authentication since a fingerprint pattern changes over time due to the compression. The method and the device of the present invention may additionally comprise a method/means for carrying out authentication of a living body by such a compression mechanism.

EXAMPLES

Figure 5:
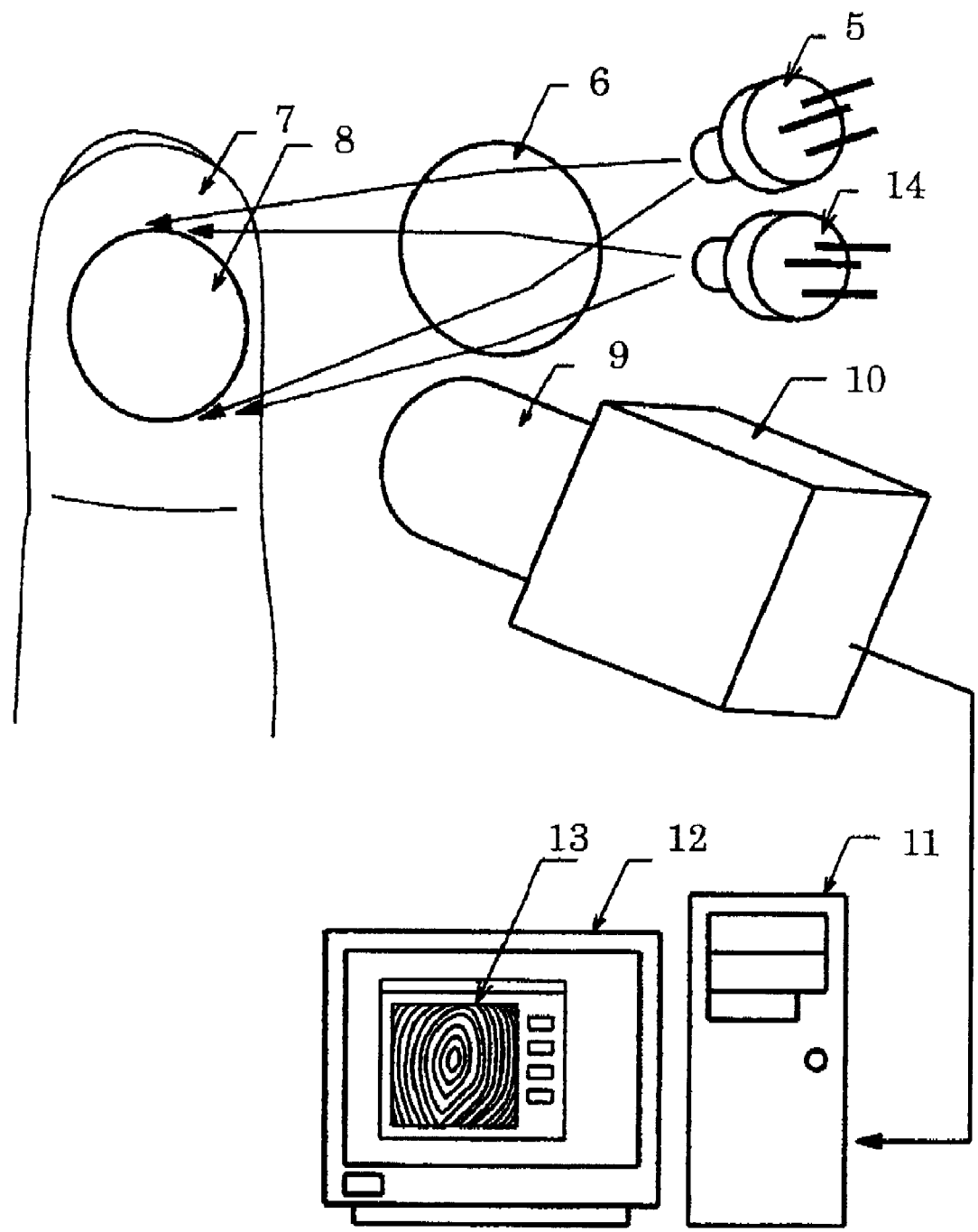

FIG. 5 is one example of the device of the present invention, 5 denotes a near-infrared semiconductor laser, 6 denotes an irradiation optical system, 7 denotes a finger pad, 8 denotes a laser spot, 9 denotes an imaging lens, 10 denotes an image sensor, 11 denotes an analytical personal computer, 12 denotes a display, 13 denotes a finger pad blood flow map, and 14 denotes a visible light semiconductor laser.

A laser beam scattered from the finger pad forms a random interference stripe pattern (laser speckle) on the image sensor, and a finger pad blood flow map is obtained as a two-dimensional map by analyzing and processing the stripe pattern by a personal computer. This blood flow map is observed on the display 12 as shown by 13 in FIG. 5.

When the near-infrared semiconductor laser 5 is switched on, light scattered internally from the surface of the finger reaches a blood vessel layer in a subcutaneous deep portion, and a sea-island like blood flow map (which can be colorized) showing unevenness as in FIG. 3 reflecting a blood flow distribution of the skin interior or the pulse is obtained on the display. This map is divided into, for example, 16 regions as in FIG. 4, and an average blood flow value of each region or an amplitude, waveform, etc. of change over time is determined, thus giving data characteristic of an individual. It is therefore possible to authenticate an individual by comparison-checking these data against pre-registered data of individuals.

Furthermore, if the visible light semiconductor laser 14 is used together with the near-infrared semiconductor laser 5 by, for example, switching on these two lasers separately, blood flow maps corresponding to their respective wavelengths are obtained, and it is thus possible to obtain two images in sequence, that is, blood flow data as shown in FIG. 3 in which unevenness of blood flow characteristic of an individual is superimposed and data as shown in FIG. 2 in which only a fingerprint is clearly imaged. It is therefore possible to constitute a more robust personal authentication system by combining a fingerprint pattern obtained from a visible light semiconductor laser with a blood flow distribution of a subcutaneous deep portion or nonuniformities in the variation thereof over time characteristic of an individual visualized in a blood flow image obtained from a near-infrared semiconductor laser.

INDUSTRIAL APPLICABILITY

The personal authentication system in accordance with the present invention combines a sophisticated fingerprint pattern with biometric information, and forgery is therefore difficult. Utilizing this advantage enables its utilization in immigration control or room entrance/exit surveillance where a high degree of security control is required.

What is claimed is:

1. A personal authentication method comprising imaging, on an image sensor as a laser speckle using an optical system, light reflected from a blood vessel layer in subcutaneous and internal tissues when a laser beam is expanded and made to irradiate a finger pad, calculating a quantity that represents the rate of change with respect to time of the amount of light received for each pixel of the laser speckle, obtaining a finger pad blood flow map as a two-dimensional map of the numerical values, and comparison-checking the blood flow map against pre-registered data of individuals, wherein using a near-infrared laser beam, which can reach the internal tissue of the finger pad, and a visible laser beam, which is easily absorbed by the subcutaneous stratum corneum, finger pad blood flow maps obtained from the respective reflected lights are measured at the same time or in sequence, and the two types of blood flow maps thus obtained are comparison-checked against pre-registered data of individuals.

2. The personal authentication method according to claim 1, wherein the near-infrared laser light has a wavelength in the range of about 770 to 1200 nm.

3. The personal authentication method according to claim 1, wherein the visible laser light has a wavelength in the range of about 380 to 770 nm.

4. The personal authentication method according to claim 2, wherein the visible laser light has a wavelength in the range of about 380 to 770 nm.

* * * * *